United States Patent [19]

DeWille et al.

[11] Patent Number: 5,514,655
[45] Date of Patent: * May 7, 1996

[54] ENTERAL NUTRITIONAL WITH PROTEIN SYSTEM CONTAINING SOY PROTEIN HYDROLYSATE AND INTACT PROTEIN

[75] Inventors: Normanella T. DeWille, Upper Arlington; Terrence B. Mazer, Reynoldsbury; Gregory A. Snowden, Pickerington, all of Ohio

[73] Assignee: Abbott Laboratories, Abbott Park, Ill.

[*] Notice: The portion of the term of this patent subsequent to Apr. 4, 2012, has been disclaimed.

[21] Appl. No.: 68,449

[22] Filed: May 28, 1993

[51] Int. Cl.⁶ .............................. A23J 3/16; A23L 1/052; A61K 38/17; A61K 47/42
[52] U.S. Cl. ................. 514/21; 514/2; 426/654; 426/656; 426/657
[58] Field of Search .................. 514/21, 2; 426/46, 426/656, 657, 648, 654

[56] References Cited

U.S. PATENT DOCUMENTS

| | | | |
|---|---|---|---|
| 4,100,024 | 7/1978 | Adler-Nissen | 195/29 |
| 4,159,952 | 7/1979 | Jackson | 426/654 |
| 4,850,704 | 7/1989 | Zimmerly et al. | 366/263 |
| 4,954,350 | 8/1990 | Frokjaer | 514/2 |
| 5,221,668 | 6/1993 | Henningfield et al. | 514/2 |
| 5,308,832 | 5/1994 | Garleb et al. | 514/2 |

FOREIGN PATENT DOCUMENTS

| | | |
|---|---|---|
| 246747 | 10/1989 | European Pat. Off. |
| 59-045854 | 8/1984 | Japan |
| 60-251840 | 12/1986 | Japan |
| WO91/13554 | 9/1991 | WIPO |
| WO92/18015 | 10/1992 | WIPO |

OTHER PUBLICATIONS

Food Chemistry Second Edition, Revised and Expanded, edited by O. Fennema, Marcel Dekker, Inc., (1985), pp. 246–247, 282–283, 817.

*Primary Examiner*—Chhaya D. Sayala
*Attorney, Agent, or Firm*—Lonnie R. Drayer

[57] ABSTRACT

A liquid enteral nutritional product contains a protein system of, by weight, about 50–90% of a soy protein hydrolysate having a degree of hydrolysis in the range of 14 to 17% and not more than 50% of one or more intact protein sources. The nutritional product may also contain an emulsifier, Iota carrageenan and Kappa carrageenan.

13 Claims, No Drawings

ENTERAL NUTRITIONAL WITH PROTEIN SYSTEM CONTAINING SOY PROTEIN HYDROLYSATE AND INTACT PROTEIN

The present invention relates generally to liquid nutritional products for enteral consumption and more specifically to such nutritional products which contain a partially hydrolyzed vegetable protein and intact vegetable protein.

It is believed to be medically advantageous to provide an enteral liquid nutritional product having a source of protein comprising a soy protein hydrolysate of the type manufactured using a process taught in U.S. Pat. No. 4,100,024, which is incorporated herein for the purpose of teaching a process for manufacturing a soy protein hydrolysate for use in the practice of the present invention. Briefly, this process for the preparation of polypeptides from soy protein soluble in an aqueous media at pH's in the range of 2 to 7 involves: hydrolyzing soy protein with a microbial, alkaline proteinase in a concentration ranging from 4 to 25 Anson units per kg of soy protein at a substrate concentration of between 5 and 20% w/w soy protein, at a pH in the range of from 7.5 to 8.5, until a degree of hydrolysis in the range of from about 8 to 15% is attained, whereafter the enzyme is inactivated by reduction of pH with a food grade acid, then recovering the supernatant from the precipitate. However, it is understood that a soy protein hydrolysate produced by any other process which has the characteristics elaborated upon herein may be used in the practice of the present invention.

An example of a nutritional product containing such a soy protein hydrolysate is taught in U.S. Pat. No. 4,959,350, but this prior art nutritional product has a pH of lower than 4.5 (as compared to a pH of 6.4 to 6.6 in the product of the present invention).

The nutritional product of the present invention has been manufactured using soy protein hydrolysate (SPH) obtained from NOVO Industri A/S, Bagsvaerd, Denmark, (NOVO) manufactured according to the above described process. The properties of a soy protein hydrolysate which is suitable for use in the practice of the present invention have been determined by actual analysis of samples from several lots of soy protein hydrolysate obtained from NOVO Industri and/or specifications selected in accordance with desired properties.

Per the manufacturer's specifications SPH obtained from NOVO comprises by weight, not less than 76%, preferably not less than 80% protein, not more than 1% fat, and not more than 5.5%, preferably not more than 4.8% ash. A 5% slurry (by weight) of the soy protein hydrolysate in water has a pH in the range of about 4.2 to 4.3, but in any instance less than 4.5. The degree of hydrolysis (DH) of the soy protein hydrolysate (AN/TN×100) is in the range of about 14 to 17 and most preferably about 16.

The amino acid profile of the soy protein hydrolysate that has been used in the practice of the present invention is presented in Table 1, and the mineral profile is presented in Table 2. The molecular weight profile is presented in Table 3 for soy protein hydrolysate (SPH) having about a degree of hydrolysis of 16 with the approximate molecular weight partition determined by size exclusion chromatography of samples from 4 lots of SPH. The molecular weight profile of the soy protein hydrolysate is believed to be very important because the particles sizes are related to their physical activity and product functionality. That is to say, for the SPH used in the practice product of the present invention the molecular weight profile indicates a large peptide content (molecular weights of 1500–5000) and a small free amino acid content (less than 1 g of free amino acids per 100 g SPH). The mineral profile of the soy protein hydrolysate is believed to be very important because it supplies most of the trace and ultratrace minerals in the nutritional product.

TABLE 1

AMINO ACID PROFILE OF SOY PROTEIN HYDROLYSATE (g/100 g)

| Amino Acid | g/100 g |
| --- | --- |
| Aspartic acid | 9.8–10.4 |
| Threonine | 2.9–3.2 |
| Serine | 3.7–4.4 |
| Glutamic Acid | 17.0–18.1 |
| Proline | 4.4–4.9 |
| Glycine | 3.2–3.3 |
| Alanine | 3.0–3.2 |
| Valine | 2.9–3.6 |
| Methionine | 0.9–1.1 |
| Isoleucine | 3.0–3.7 |
| Leucine | 5.1–5.3 |
| Tyrosine | 2.7–2.9 |
| Phenylalanine | 3.3–3.5 |
| Histidine | 2.0–2.2 |
| Lysine | 5.5–5.8 |
| Arginine | 6.3–6.7 |
| Tryptophan | 0.3–0.7 |
| Cystine | 1.3–1.4 |
| Free Amino Acids | 0.4–0.7 |

TABLE 2

MINERAL PROFILE OF SOY PROTEIN HYDROLYSATE

| | Preferred Range | Most Preferred Range |
| --- | --- | --- |
| Calcium, mg/100 g | 170–350 | 170–260 |
| Sodium, mg/100 g | 370–650 | 370–520 |
| Potassium, mg/100 g | 180–600 | 180–470 |
| Magnesium, mg/100 g | 270–550 | 270–400 |
| Phosphorus, mg/100 g | 900–1500 | 900–1200 |
| Chloride, mg/100 g | 1400–2500 | 1400–2250 |
| Iron, mg/100 g | 13–25 | 13–20 |
| Zinc, mg/100 g | 3–6 | 3–6 |
| Manganese, mg/100 g | 4–8 | 5–7 |
| Copper, mg/100 g | 0.5–1.5 | 0.5–1.0 |
| Vanadium, ppm | trace–15 | 8–12 |
| Selenium, ppb | trace–350 | 150–300 |
| Chromium, ppm | trace–2.9 | 1.5–2.3 |
| Molybdenum, ppm | trace–3.7 | 2–3 |

TABLE 3

MOLECULAR WEIGHT PARTITION FOR SPH (AS DETERMINED BY SIZE EXCLUSION CHROMATOGRAPHY OF SAMPLES FROM FOUR DIFFERENT LOTS OF SPH)

| | % of Particles With This Molecular Wt. | | |
| --- | --- | --- | --- |
| Molecular Wt. (in Daltons) | Average | Std. Deviation | Range |
| >5000 | 3.3 | 1.96 | 1.70–5.96 |
| 2000–5000 | 25.8 | 5.42 | 19.50–30.75 |
| 1500–2000 | 20.5 | 7.41 | 13.10–27.50 |
| 1200–1500 | 12.5 | 0.92 | 11.80–13.80 |
| 1000–1200 | 8.2 | 0.83 | 7.30–9.00 |
| 500–1000 | 19.5 | 3.02 | 16.80–23.80 |

TABLE 3-continued

MOLECULAR WEIGHT PARTITION FOR SPH
(AS DETERMINED BY SIZE EXCLUSION
CHROMATOGRAPHY OF SAMPLES
FROM FOUR DIFFERENT LOTS OF SPH)

| Molecular Wt. (in Daltons) | % of Particles With This Molecular Wt. | | |
|---|---|---|---|
| | Average | Std. Deviation | Range |
| <500 | 10.2 | 6.03 | 5.30–19.00 |

Preferably the soy protein hydrolysate used in the practice of the present invention has a degree of hydrolysis in the range of 14 to 17 and a molecular weight partition as determined by size exclusion chromatography wherein 30–60% of the particles have a molecular weight in the range of 1500–5000 Daltons and the amino acid profile of the soy protein hydrolysate has less than 1% free amino acids.

It was discovered that the soy protein hydrolysate used in the protein system and emulsion of the present invention does not yield a shelf stable product in the absence of intact protein. Once a protein is hydrolyzed, it looses its primary and secondary structure and consequently some of its functionality, including emulsifying properties. Therefore, it does not have surfactant properties and is unable to stabilize the formulation resulting in phase separation. Various approaches were investigated to attempt to stabilize a liquid product containing this particular soy protein hydrolysate: (a) the use of starches, (b) the use of emulsifiers, and (c) the use of intact proteins. Three different emulsifiers, and combinations thereof, were evaluated, but the most effective emulsifier is Panodan® which is distributed by GRINSTED of Danisco, Denmark. Panodan® is diacetyl tartaric acid esters of monodiglycerides and is an anionic surfactant with a very hydrophilic component attached. Panodan® is generally regarded as safe (GRAS) for use in nutritional products for human consumption. Panodan® works by imparting a negative charge to the fat globules, thus, causing them to electrostatically repel each other so that no flocculation or coalescence occurs. The soy protein hydrolysate could stay in an emulsion for about two weeks with Panodan®, but no other protein source present. It is believed that sodium stearoyl lactoylate could also be used as an emulsifier, but this emulsifier has not been classified as GRAS by the U.S. Food and Drug Administration.

The use of starches to stabilize an emulsion containing the soy protein hydrolysate was investigated, but this approach was abandoned because the viscosity of the emulsion was too high.

The use of intact proteins as a stabilizer was also investigated. Caseinates, for example, have a high electrical charge that make them hydrophilic and have several hydrophobic groups. This, and their random coiled molecular structure, makes them ideal emulsifiers with a strong preference for fat/water interfaces. It was discovered that a protein system comprising, by weight, at least 10–30% sodium caseinate with the remainder being the soy protein hydrolysate described herein, in combination with Panodan® yielded an emulsion having satisfactory stability with regards to phase separation throughout shelf-life (12–15 months).

The protein system in a preferred embodiment of the present invention comprises, by weight, about 78% soy protein hydrolysate and about 22% sodium caseinate. However, it is understood that any suitable intact protein, such as pea protein and/or whey protein concentrate may be used in the practice of the present invention.

The protein system was evaluated in emulsions manufactured by combining an oil blend containing oils, oil soluble vitamins, and emulsifiers with a mineral/carbohydrate/protein blend containing the soy protein hydrolysate, fiber, minerals, and simple and complex carbohydrates. The final blend was pH adjusted and processed using UHT treatment and two-stage homogenization at 4000/500 PSIG. The details of manufacturing such a product are set forth below with reference to Table 12. The ingredients used in these experimental emulsions are listed in Table 4.

TABLE 4

BILL OF MATERIALS FOR FORMULA
USED IN EXPERIMENTS

| COMPONENT | AMOUNT PER 1,000 kg (in kg) |
|---|---|
| Canola | 17.2 |
| MCT Oil | 4.14 |
| Emulsifier (Varied) | Varied |
| Oil Soluble Vitamins Premix | 0.0585 |
| Alpha-tocopheryl Acetate | 0.04299 |
| Vitamin A Palmitate | 0.003574 |
| Phylloquinone | 0.000079 |
| Vitamin D3 | 0.0000097 |
| Coconut Oil (carrier) | Q.S. |
| β-Carotene | 0.0188 |
| Alternate Protein (Varied) | 13.34 |
| Water | 703.32 |
| Sucrose | 42.27 |
| Complex Carbohydrate (Varied) | Varied |
| Sodium Citrate | 1.47 |
| Magnesium Phosphate dibasic | 0.461 |
| Tricalcium Phosphate (preferably ultramicronized) | 0.060 |
| Calcium Carbonate | 1.61 |
| Soy protein Hydrolysate | Varied |
| 45% KOH (proc. Aid) | 5.17 |
| Soy Polysaccharides | 9.92 |
| Iota Carrageenan | Varied |
| Kappa Carrageenan | Varied |
| Ferrous Sulfate | 0.03476 |
| Manganous Sulfate | 0.0062 |
| Copper Sulfate | 0.0098 |
| Sodium Selenate | 0.00014 |
| Zinc Sulfate | 0.07035 |
| Water Soluble Vitamin Premix | 0.0875 |
| Niacinamide | 0.03286 |
| d-Calcium Pantothenate | 0.02126 |
| Pyridoxine Hydrochloride | 0.00522 |
| Thiamine Hydrochloride | 0.00543 |
| Riboflavin | 0.00424 |
| Folic Acid | 0.00074 |
| Biotin | 0.00064 |
| Cyanocobalamin | 0.000014 |
| Dextrose (carrier) | Q.S. |
| Taurine | 0.1946 |
| L-Carnitine | 0.146 |
| Choline Chloride | 0.266 |
| Ascorbic Acid | 0.724 |

During the feasibility and optimization phases of the development of the protein system of the present invention, special attention was given to physical stability parameters, including: visual examination, viscosity, protein stability (grain), Agtron Color, fat globule size distribution, and rheological profile. Visual examination refers to the evaluation of product for overall appearance, phase separation, clear whey on top or bottom, creaming, and color. Grain is a measure of protein stability and emulsion quality wherein the product is examined in a loop and ranked depending on its smooth, creamy appearance on a scale of 1–6 where 1=best and 6=worst. Color is measured using light reflectance with the lower value corresponding to a darker product. Fat globule size is measured using a Coulter N4

(hereafter referred to simply as "N4") which is a submicron particle size analyzer consisting of a laser scanner for use in fine emulsions. In general, a smaller fat globule size is an indicator of a better emulsion. The rheological profile is determined using a Carri-Med Rheometer which can measure complete rheological profiles of products even at very low shear rates. This measurement can be useful to understand behavior during processing and storage.

The first experiments, the results of which are presented in Table 5, were designed to evaluate the emulsifying capacity of SPH and the need, if any, for an emulsifier. Batches were manufactured using SPH, with and without 5% PANODAN® as the emulsifier. PANODAN® is a strong emulsifier, very effective in systems with hydrolyzed proteins and thus, poor emulsion stability. N4 results which are a measure of fat globule size indicated that products with emulsifier had smaller fat globules.

The physical stability of the products with SPH was still considerably poorer than that desired. This was likely due to the degree of hydrolysis (DH=AN/TN×100) of SPH which is approximately 16%. When a protein is hydrolyzed it loses its primary and secondary structure and thus some of its functionality, including emulsifying properties. Consequently, it is unable to stabilize an oil in water emulsion resulting in phase separation.

TABLE 5

EXPERIMENTS TO EVALUATE EMULSION CAPACITY OF PROTEINS IN EXPERIMENTAL FORMULATIONS

| Batch No. | Protein | Emulsifier | Agtron Color | N4, nm | Viscosity cps. | Visual Examination |
|---|---|---|---|---|---|---|
| 1 | 100% SPH | 5% PANODAN® | 20.7 | 3,730 | 46.5 | Slight Separation |
| 2 | 100% SPH | 0% | 19.6 | * | 40.8 | More separated than Batch 1 |

*Fat globule size too large to be measured by N4.

Starches can impart to a liquid product the needed viscosity to minimize the tendency for the dispersed phase to destabilize or separate out. A series of experiments were conducted to evaluate the use of 1% corn starch (Salioca 448 from American Maize; Hammond, Ind.) in the formulation containing the SPH. The liquid nutritional product taught in U.S. Pat. No. 4,959,350 has a pH ranging from 4.0 to 5.0 and was described as a stable emulsion, so the effect of pH on the formulation of the present invention was also investigated.

Results are presented in Table 6. As expected, the viscosity of the products was higher when the corn starch was used. These products were more stable than the products with no starch added. The color was also better in the products with starch, a possible indication of a better emulsion. The best products were the ones at high pH (around 6.7) and containing starch. They had some clear whey, probably due to syneresis. The two variables at pH 6.7 were put in a long-term testing protocol. After 30 days, the viscosities had become higher than 100 cps; therefore, it was decided that the use of starches was not the best approach for stabilization of a liquid nutritional product containing SPH.

TABLE 6

EXPERIMENTS TO EVALUATE THE USE OF STARCH AS A STABILIZER AID IN EXPERIMENTAL FORMULATIONS MANUFACTURED AT VARIOUS pH VALUES

| Batch No. | Protein | pH | % Corn Starch | Agtron Color | N4, nm | Viscosity, cps. |
|---|---|---|---|---|---|---|
| 3 | 100% SPH | 4.9 | Yes | 12.0 | 1500 | 76.1 |
| 4 | 100% SPH | 5.2 | Yes | 12.4 | * | 74.2 |
| 5 | 100% SPH | 6.7 | Yes | 19.4 | * | 79.7 |
| 6 | 100% SPH | 4.9 | No | 12.4 | * | 60.8 |
| 7 | 100% SPH | 5.2 | No | 10.9 | * | 53.4 |
| 8 | 100% SPH | 6.7 | No | 22.6 | 5740 | 62.5 |

*Fat globule size too large to be measured by N4.

Two complex carbohydrates of shorter length that were less viscous than corn starch were also investigated, along with acid thin tapioca starch. Lodex® 15, distributed by American Maize and Maltrin 40, distributed by Grain Processing Company of Muscatine, Iowa, gave lower viscosity to the formula than the acid thin tapioca starch which produced a formula with consistency similar to pudding. Products with Maltrin® 40 were more viscous than those with Lodex® 15. This is understandable since Maltrin®40 has a lower dextrose equivalent (DE=4) than Lodex®15 (DE=15 to 18). Although the physical appearance of the product with Maltrin®40 was better than that of product with Lodex®15, the high viscosity of the former was ruled unacceptable. The results of these experiments are presented in Table 7. At this point, a decision was made to keep in the formulation a combination of Lodex®15 and sucrose, and to pursue other ways of stabilizing the emulsion such as the use of emulsifiers and other less hydrolyzed proteins.

TABLE 7

EXPERIMENTS TO EVALUATE THE USE OF OTHER COMPLEX CARBOHYDRATES AND STARCHES IN EXPERIMENTAL FORMULATIONS

| Batch No. | Protein | Complex Carbohydrate | PANODAN® | Agtron Color | Viscosity, cps. | Whey Layer, mm |
|---|---|---|---|---|---|---|
| 9 | SPH | Lodex 15 | 5% | 10.4 | 69.2 | 10 |
| 10 | SPH | Lodex 15 | 0% | 10.4 | 81.5 | 12 |
| 11 | SPH | Acid Thin Tapioca | 5% | Too thick to process | | |
| 12 | SPH | Acid Thin Tapioca | 0% | Too thick to process | | |
| 13 | SPH | Maltrin 40 | 5% | 13.9 | 151.0 | 12 |

TABLE 7-continued

EXPERIMENTS TO EVALUATE THE USE OF OTHER COMPLEX CARBOHYDRATES AND STARCHES IN EXPERIMENTAL FORMULATIONS

| Batch No. | Protein | Complex Carbohydrate | PANODAN ® | Agtron Color | Viscosity, cps. | Whey Layer, mm |
|---|---|---|---|---|---|---|
| 14 | SPH | Maltrin 40 | 0% | 19.6 | 177.0 | 15 |

30% of carbohydrate is complex-remainder is sucrose.

Three emulsifiers and combinations of them were screened: lecithin, mono-diglycerides, and diacetyl tartaric acid esters of mono-diglycerides (PANODAN®). These are the only food emulsifiers with GRAS status. PANODAN® was the most effective, and it could hold an emulsion for about two weeks before wheying-off and did not show signs of free fat. PANODAN® is an ionic surfactant with a very hydrophilic component (a carboxylic acid) attached. PANODAN® works by imparting a negative charge to the fat globules, thus causing them to electrostatically repel each other so that flocculation or coalescence does not occur. The results of these experiments are presented in Table 8.

TABLE 8

EXPERIMENTS TO EVALUATE VARIOUS EMULSIFIERS IN EXPERIMENTAL FORMULATIONS

| Batch No. | Protein | Second Protein | Emulsifier | Viscosity cps. | Whey Layer mm, Initial | Whey Layer mm, 90 Days | Visual Examination |
|---|---|---|---|---|---|---|---|
| 15 | 100% SPH | 0% | 6% PANODAN ® | 40.5 | Trace | 30 | Not good, wheying off |
| 16 | 100% SPH | 0% | 3% L 3% M | 39.6 | 6 | 15 | Not good, wheying off |
| 17 | 100% SPH | 0% | 6% L | 37.0 | 10 | 35 | Not good, wheying off |
| 18 | 100% SPH | 0% | 6% M | 40.6 | 10 | 6 | Not good, wheying off |
| 19 | 90% SPH | 10% FXP720 | 6% PANODAN ® | 55.0 | Trace | 19 | Wheying off on top, white specs |
| 20 | 90% SPH | 10% FXP720 | 3% L 3% M | 48.9 | Trace | 22 | Wheying off on top, white specs |
| 21 | 90% SPH | 10% FXP720 | 6% L | 48.2 | Trace | — | Wheying off on top, not good |
| 22 | 90% SPH | 10% FXP720 | 6% M | 48.9 | Trace | 26 | Wheying off on top |
| 23 | 85% SPH | 16% FXP720 | 6% PANODAN ® | 57.1 | Trace | 23 | Wheying off on top, slightly better |
| 24 | 85% SPH | 16% FXP720 | 3% L 3% M | 54.3 | Trace | — | Wheying off on top |
| 25 | 85% SPH | 16% FXP720 | 6% L | 48.2 | Trace | — | Wheying off on top |
| 26 | 85% SPH | 16% FXP720 | 6% L | 47.8 | Trace | — | Wheying off on top |

TABLE 8-continued

EXPERIMENTS TO EVALUATE VARIOUS EMULSIFIERS IN
EXPERIMENTAL FORMULATIONS

| Batch No. | Protein | Second Protein | Emulsifier | Viscosity cps. | Whey Layer mm, Initial | Whey Layer mm, 90 Days | Visual Examination |
|---|---|---|---|---|---|---|---|

L = Lecithin
M = Myverol (mono-diglycerides)

Many enteral liquid nutritional products are protein-stabilized emulsions with significant quantities of additional protein in the bulk phase. An attempt was made to stabilize the emulsion by substituting a less hydrolyzed protein for a small percentage of the SPH. The proteins investigated were FXP 720 (DH=10) and PP750 (DH=1–2), less hydrolyzed soy protein hydrolysates from Protein Technologies International (PTI) of St. Louis, Mo. USA. PP1610, a soy protein isolate, and sodium caseinate were also investigated. Results of various experiments are shown in Table 9. Products with slightly better than FXP720. The whey layer in the products containing sodium caseinate was milky and almost indistinguishable. Caseinates have a high electrical charge that makes them hydrophilic and have several hydrophobic regions. This and their random coiled molecular structure makes them ideal emulsifiers with a strong preference for fat/water interfaces. From this work it was concluded that sodium caseinate had the most stabilizing power and was the protein of choice to complement SPH in a liquid nutritional product.

TABLE 9

EXPERIMENTS TO EVALUATE VARIOUS PROTEIN COMBINATIONS
IN EXPERIMENTAL FORMULATIONS

| Batch No. | Protein | Second Protein | Third Protein | Emulsifier | Viscosity Initial | Viscosity 90 Days | Whey Layer mm Initial | Whey Layer mm 90 Days | Grain |
|---|---|---|---|---|---|---|---|---|---|
| 27 | 100% SPH | — | — | 5% *P | 57.5 | 63.6 | 1 | 2 | Not possible |
| 28 | 75% SPH | 25% PP750 | — | 5% *P | 84.7 | 86.2 | 2 | 20 | Not possible |
| 29 | 100% PP750 | — | — | 5% *P | 142 | 137 | 0 | 21 | Not possible |
| 30 | 90% SPH | 10% NaCas | — | 0% | 64.2 | 91.3 | Trace | 3 | Not possible |
| 31 | 85% SPH | 15% NaCas | — | 5% *P | 29.7 | NA | Trace | NA | 1 |
| 32 | 85% SPH | 15% NaCas | — | 3% *P | 34.3 | NA | Trace | NA | 1 |
| 33 | 80% SPH | 10% NaCas | 10% FXP720 | 6% *P | 54.5 | 55.4 | Trace | 24 | 5 |
| 34 | 80% SPH | 10% NaCas | 10% FXP720 | 3% *P | 44.9 | 50.6 | Trace | 27 | 5 |
| 35 | 80% SPH | 20% NaCas | — | 6% *P | 35.9 | 41.1 | Trace | 5 | 1 |
| 36 | 80% SPH | 20% NaCas | — | 3% *P | 68.1 | 176 | Trace | 15 | 5 |
| 37 | 70% SPH | 20% NaCas | 10% PP1610 | 6% *P | 37.4 | 191 | Trace | 0 | 5 |
| 38 | 70% SPH | 20% NaCas | 10% PP1610 | 3% *P | 65.8 | 91.1 | Trace | 16 | 5 |
| 39 | 70% SPH | 20% NaCas | 10% FXP720 | 6% *P | 76.1 | 147 | Trace | 22 | 6 |
| 40 | 70% SPH | 20% NaCas | 10% FXP720 | 3% *P | 82.8 | 166 | Trace | 22 | 6 |

NA = not available
*P = PANODAN® as % by weight of total fat

PP750 by itself or in combination showed signs of syneresis or clear whey expelled from the product and very high viscosities. Only when sodium caseinate was incorporated in the formulation was the emulsion stable enough that a loop could be pooled for grain reading. Better grains were seen in products containing SPH and sodium caseinate without a third protein such as FXP720 and PP1610. PP1610 was Once the most effective approaches to emulsion stability were identified, an optimization study was initiated. Five variables were investigated using a D-optimal experimental design: (a) Sodium caseinate level; (b) Third protein level; (c) PANODAN® level; (d) Carrageenan type; (e) Carrageenan level. Sodium caseinate was optimized to a minimum level because it was not known at the time if sodium caseinate, a milk protein, counteracted the trophic effect of the SPH. PANODAN® was also optimized to a minimum level to avoid regulatory issues overseas where there is a maximum usage level for this ingredient. Carrageenans were investigated as stabilizer sources to attempt to reduce the milky whey layer observed in the product. The responses evaluated were clear or milky phase separation, viscosity, fat globule size (N4), and rheological behavior (Yield Value). The results are summarized in Table 10A, 10B, and 10C. Products with sodium caseinate and no third protein added appeared to have the best emulsion quality as indicated by lower grain values. If a third protein had to be used, PP1610 was superior to FXP720. Ten to thirty percent was the minimum effective range for sodium caseinate. In general, good emulsions as measured by fat globule size (N4) were those containing sodium caseinate and a high level of emulsifier. Products with carrageenan were better than those with no carrageenan, and kappa carrageenan caused higher viscosity than iota carrageenan.

TABLE 10A

OPTIMIZATION RESULTS FOR FORMULATION

| Batch No. | Variable* | Viscosity (cps) | Clear Whey (mm) | N4 (nm) | Yield | Grain |
|---|---|---|---|---|---|---|
| 41 | 10% NaCas, 0% PP1610, 6% Pan, 0 ppm Kappa | 18.7 | 0 | 485 | 0.1930 | 5 |
| 42 | 10% NaCas, 0% FXP720, 6% Pan, 600 ppm Iota | 23.7 | 0 | 409 | 0.7632 | 5 |
| 43 | 30% NaCas, 0% FXP720, 6% Pan, 400 ppm Kappa | 56.7 | 0 | 200 | 1.119 | 1 |
| 44 | 10% NaCas, 0% PP1610, 3% Pan, 600 ppm Kappa | 85.8 | 6 | 23200 | 0.4412 | 6 |
| 45 | 20% NaCas, 10% PP1610, 6% Pan, 600 ppm Kappa | 82.4 | 0 | 581 | 0.3964 | 5 |
| 46 | 30% NaCas, 0% PP1610, 6% Pan, 0 ppm Iota | 21.9 | 0 | 189 | 0.3265 | 1 |
| 47 | 30% NaCas, 0% PP1610, 3% Pan, 0 ppm Kappa | 19.6 | 0 | 205 | 0.3888 | 1 |
| 48 | 15% NaCas, 10% PP1610, 6% Pan, 300 ppm Iota | 25.3 | 9 | 18900 | 0.1623 | 5 |
| 49 | 30% NaCas, 10% PP1610, 3% Pan, 0 ppm Iode | 21.9 | 0 | 463 | 0.1950 | 1 |
| 50 | 10% NaCas, 5% FXP720, 3% Pan, 0 ppm Iode | 24.3 | 14 | 26700 | 0.5287 | 6 |
| 51 | 20% NaCas, 5% PP1610, 3% Pan, 700 ppm Iode | 26.8 | 0 | 1220 | 0.4007 | 1 |
| 52 | 30% NaCas, 10% FXP720, 7% Pan, 0 ppm Kappa | 26.6 | 0 | 500 | 0.8424 | 1 |

*NaCa, PP1610, and FXP720 are given as % by weight of protein, with the remainder of protein being SPH; Panodan (Pan) is given as % by weight of total fat in the formulation; and Kappa Carrageenan (Kappa) and Iota Carrageenan (Iota) are presented as ppm formulation.

TABLE 10B

OPTIMIZATION RESULTS FOR FORMULATION

| Batch No. | Variable* | Viscosity (cps) | Clear Whey (mm) | N4 (nm) | Yield | Grain |
|---|---|---|---|---|---|---|
| 53 | 10% NaCas, 10% PP1610, 3% Pan, 700 ppm Kappa | 69.6 | 14 | 17300 | 0.9646 | 5 |
| 54 | 30% NaCas, 10% FXP720, 3% Pan, 600 ppm Iode | 85.1 | 10 | 48000 | 2.307 | 6 |
| 55 | 10% NaCas, 5% PP1610, 6% Pan, 400 ppm Kappa | 54.0 | 5 | 19600 | 0.8681 | 5 |
| 56 | 10% NaCas, 10% FXP720, 6% Pan, 0 ppm Kappa | 44.7 | 5 | 18100 | 1.018 | 5 |
| 57 | 10% NaCas, 10% FXP720, 3% Pan, 0 ppm Kappa | 42.3 | 10 | 24900 | 0.8183 | 6 |
| 58 | 30% NaCas, 0% FXP720, 3% Pan, 0 ppm Iode | 29.5 | 0 | 297 | 0.8649 | 1 |
| 59 | 10% NaCas, 0% FXP720, 3% Pan, 600 ppm Kappa | 153.0 | 0 | 929 | 0.8819 | 1 |
| 60 | 30% NaCas, 10% FXP720, 7% Pan, 600 ppm Kappa | 141.0 | 3 | 23900 | 0.8183 | 5 |
| 61 | 15% NaCas, 10% PP1610, 4.5% Pan, 300 ppm Kappa | 82.3 | 2 | 24900 | 0.5342 | 5 |
| 62 | 15% NaCas, 10% PP1610, 4.5% Pan, 300 ppm Kappa | 81.3 | 2 | 25300 | 0.8056 | 5 |
| 63 | 15% NaCas, 10% PP1610, 4.5% Pan, 300 ppm Kappa | 83.3 | 2 | 24500 | 0.9497 | 5 |
| 64 | 30% NaCas, 10% PP1610, 6% Pan, 700 ppm Iode | 98.2 | 5 | 17000 | 1.215 | 5 |

*NaCa, PP1610, and FXP720 are given as % by weight of protein, with the remainder of protein being SPH; Panodan (Pan) is given as % by weight of total fat in the formulation; and Kappa Carrageenan (Kappa) and Iota Carrageenan (Iota) are presented as ppm formulation.

TABLE 10C

OPTIMIZATION RESULTS FOR FORMULATION

| Batch No. | Variable* | Viscosity (cps) | Clear Whey (mm) | N4 (nm) | Yield | Grain |
|---|---|---|---|---|---|---|
| 65 | 30% NaCas, 10% FXP720, 3% Pan, 0 ppm Kappa | 69.9 | 3 | 41500 | 1.262 | 6 |
| 66 | 10% NaCas, 0% FXP720, 6% Pan, 0 ppm Kappa | 85.1 | 3 | 21800 | 1.215 | 1 |
| 67 | 30% NaCas, 10% PP1610, 7% Pan, 0 ppm Kappa | 54.0 | 3 | 27300 | 0.8141 | 6 |
| 68 | 30% NaCas, 0% PP1610, 4% Pan, 600 ppm Kappa | 44.7 | 0 | 257 | 1.628 | 1 |
| 69 | 10% NaCas, 10% PP1610, 3% Pan, 0 ppm Kappa | 42.3 | 10 | 26200 | 1.033 | 5 |
| 70 | 10% NaCas, 0% FXP720, 3% Pan, 400 ppm Iode | 29.5 | 3 | 21200 | 1.012 | 1 |
| 71 | 30% NaCas, 10% PP1610, 3% Pan, 700 ppm Kappa | 153.0 | 5 | 13400 | 1.611 | 1 |

TABLE 10C-continued

OPTIMIZATION RESULTS FOR FORMULATION

| Batch No. | Variable* | Viscosity (cps) | Clear Whey (mm) | N4 (nm) | Yield | Grain |
|---|---|---|---|---|---|---|
| 72 | 30% NaCas, 5% FXP720, 6% Pan, 0 ppm Iode | 141.0 | 10 | 26700 | 1.611 | 5 |
| 73 | 30% NaCas, 0% PP1610, 7% Pan, 600 ppm Kappa | 82.3 | 0 | 229 | 1.085 | 1 |
| 74 | 20% NaCas, 0% PP1610, 3% Pan, 0 ppm Iode | 81.3 | 2 | 24500 | 0.430 | 5 |
| 75 | 10% NaCas, 0% PP1610, 3% Pan, 0 ppm Iode | 83.3 | 5 | 16300 | 0.6537 | 6 |
| 76 | 10% NaCas, 10% FXP720, 6% Pan, 600 ppm Kappa | 98.2 | 0 | 35200 | 1.585 | 5 |

*NaCa, PP1610, and FXP720 are given as % by weight of protein, with the remainder of protein being SPH; Panodan (Pan) is given as % by weight of total fat in the formulation; and Kappa Carrageenan (Kappa) and Iota Carrageenan (Iota) are presented as ppm formulation.

One response investigated was rheological behavior, because single point measurements of viscosity do not offer an information on flow behavior parameters which can be useful in determining pumping characteristics. The best formulations in the experimental design exhibited pseudo-plastic behavior (shear thinning) and yield value. Shear thinning behavior is desirable for good mouth feel and feeding tube flow characteristics. Yield value is a measure of resistance to flow. A high yield value is desirable so that no phase separation occurs on standing, but a minimal shear allows flow.

From the optimization study, the following levels were established for one preferred embodiment of the invention:

|  | Optimal | Range |
|---|---|---|
| SPH, % of protein | 78 | 70–90 |
| Sodium Caseinate, % of protein | 22 | 10–30 |
| PANODAN ®, % of fat | 5 | 3–6 |
| Iota Carrageenan, ppm | 350 | 300–400 |
| Kappa Carrageenan, ppm | 50 | 50–100 |

However, the present invention is understood to encompass a protein system which comprises, by weight, at least 50% of the above described soy protein hydrolysate, and at least 10% intact protein.

This formulation has been successfully replicated in numerous experimental batches ranging from 50 to 60,000 pounds in size. The best physical characteristics are obtained at the optimal level of the key ingredients. In addition to improving the emulsion quality of an enteral nutritional formulation, sodium caseinate has improved the amino acid profile of the formulation (see Table 11) and its flavor.

TABLE 11

APPROXIMATE AMINO ACID PROFILE OF FORMULA CONTAINING TWO PROTEIN SYSTEMS

| Amino Acid mg/g Protein | 100% SPH | 78/22 SPH/NaCas | Amino Acid Requirement Patterns for Adults[a] |
|---|---|---|---|
| Threonine | 38.8 | 39.7 | 9 |
| Valine | 41.3 | 40.9 | 13 |
| Isoleucine | 41.9 | 38.7 | 13 |
| Leucine | 65.0 | 70.8 | 19 |
| Phenylalanine + Tyrosine | 77.5 | 78.2 | 19 |
| Histidine | 26.2 | 26.1 | (11)[b] |
| Lysine | 71.37 | 68.6 | 16 |
| Tryptophan | 6.2 | 6.5 | 5 |
| Methionine + Cystine | 15.0 | 28.9 | 17 |

[a]From TABLE 6-5, Recommended Dietary Allowances, 10th Edition, FNB/NRC page 67.
[b]Value is imputed.

The Bill of Materials for manufacturing an enteral nutritional product according to one preferred embodiment of the present invention is presented in Table 12. It is believed that the enteral nutritional product of this preferred embodiment has utility for providing enteral nutritional support for persons infected with the human immunodeficiency virus. The procedure for manufacturing the nutritional product of this preferred embodiment is set forth immediately following Table 12. It is understood that while this particular formulation is for a chocolate flavored product, other flavors can be used and functionally equivalent ingredients may be substituted into the Bill of Materials without deviating from the scope of the invention.

TABLE 12

BILL OF MATERIALS FOR FORMULA CHOCOLATE FLAVOR PRODUCT

| COMPONENT | AMOUNT PER 1,000 kg (in kg) |
|---|---|
| Canola Oil | 14.5 |
| MCT Oil | 4.14 |
| Diacetyl Tartaric Acid Esters of | |

TABLE 12-continued

BILL OF MATERIALS FOR FORMULA CHOCOLATE FLAVOR PRODUCT

| COMPONENT | AMOUNT PER 1,000 kg (in kg) |
|---|---|
| Mono and Diglycerides (Panodan ®) | 1.07 |
| Oil Soluble Vitamins Premix | 0.0585 |
| Alpha-tocopheryl Acetate | 0.04299 |
| Vitamin A Palmitate | 0.003574 |
| Phylloquinone | 0.000079 |
| Vitamin D3 | 0.0000097 |
| Coconut Oil (carrier) | Q.S. |
| β-Carotene | 0.0188 |
| Sodium Caseinate | 13.34 |
| Water | 703.32 |
| Sucrose | 42.27 |
| Corn Syrup Solids | 131.49 |
| Sodium Citrate | 1.47 |
| Magnesium Phosphate dibasic | 0.461 |
| Tricalcium Phosphate (preferably ultramicronized) | 0.060 |
| Calcium Carbonate | 1.61 |
| Soy protein Hydrolysate | 52.87 |
| 45% KOH (proc. Aid) | 5.17 |
| Soy Polysaccharides | 9.92 |
| Iota Carrageenan | 0.3 |
| Kappa Carrageenan | 0.50 |
| Cocoa Powder | 8.0 |
| Marine Oil high omega 3 | 2.07 |
| Ferrous Sulfate | 0.03476 |
| Manganous Sulfate | 0.0062 |
| Copper Sulfate | 0.0098 |
| Sodium Selenate | 0.00014 |
| Zinc Sulfate | 0.07035 |
| Water Soluble Vitamin Premix | 0.0875 |
| Niacinamide | 0.03286 |
| d-Calcium Pantothenate | 0.02126 |
| Pyridoxine Hydrochloride | 0.00522 |
| Thiamine Hydrochloride | 0.00543 |
| Riboflavin | 0.00424 |
| Folic Acid | 0.00074 |
| Biotin | 0.00064 |
| Cyanocobalamin | 0.000014 |
| Dextrose (carrier) | Q.S. |
| Taurine | 0.1946 |
| L-Carnitine | 0.146 |
| Potassium Iodide | 0.000158 |
| Choline Chloride | 0.266 |
| Cyanocobalamin | 0.00007 |
| Ascorbic Acid | 0.724 |
| Artificial Chocolate Flavor | 1.4 |
| Artificial Fresh Cream | 3.5 |

An oil blend is prepared by adding the required amount of canola oil and MCT oil to a blend tank and heating the oils to a temperature of about 57°–68° C. (135°–155° F.) with agitation. The required quantity of the Panodan® emulsifier, (diacetyl tartaric acid esters of mono and diglycerides), is added to the heated oil blend. The oil soluble vitamins premix and beta carotene are then added and mixed well to insure proper blending.

A protein-in-fat slurry is prepared by adding to the oil blend one half of the sodium caseinate while agitation is maintained. This slurry is kept at a temperature of about 40°–46° C. (105°–115° F.) until use.

A carbohydrate slurry is prepared by weighing the appropriate amount of water in a suitable tank and heating the water to a temperature of about 68°–74° C. (155°–165° F.). Sucrose and corn syrup solids are added under agitation to make a 60% solution, but weight.

A mineral/protein slurry is prepared by weighing the appropriate amount of water and heating the water to a temperature of about 68°–74° C. (155°–165° F.). The following ingredients are dissolved/suspended in the water with agitation in the following order: sodium citrate, magnesium phosphate dibasic, tricalcium phosphate, calcium carbonate, soy protein hydrolysate and mixed well until it is completely dissolved, to yield a 27% slurry by weight. The pH of the mineral/protein slurry is then adjusted to about 5.7–6.0 with 45% KOH.

A blend is prepared by heating the appropriate amount of water to a temperature of about 57°–68° C. (135°–150° F.) and adding the remaining sodium caseinate, soy polysaccharides, iota carrageenan and kappa carrageenan. The needed amount of cocoa powder is then added and mixed well to insure homogeneity. A mixing apparatus such as the two stage blender which is described in U.S. Pat. No. 4,850,704, which is incorporated herein for the purpose of teaching appropriate equipment for practicing the invention, may be used in making this blend.

The carbohydrate slurry, the mineral/protein slurry and the protein-in-fat slurry are combined together with agitation to yield a blend having 34% solids, by weight. The pH of the blend should be in the range of 6.25–6.55. If an adjustment of pH is needed, 1N KOH or 1N citric acid are added. Prior to emulsification fish oil is metered into the blend at a constant rate such that the dispersion of fish oil is uniform throughout the blend.

The blend is emulsified, ultra-high temperature processed (299°–304° F.), then homogenized at 3900–4100/500±100 psig using 2 stage homogenizer. The processed blend is then cooled to 1°–7° C. (34°–45° F.).

A solution of vitamins, amino acids and minerals containing about 9.0% solids by weight, is prepared by heating the appropriate amount of defluoridized water to a temperature of about 43°–54° C. (110°–130° F.). The minerals are then added with agitation, preferably in the following order: ferrous sulfate, manganous sulfate, copper sulfate, sodium selenate and zinc sulfate. The vitamins and amino acids are added with agitation in the following order: water soluble vitamin premix, taurine, L-carnitine, potassium iodide, choline chloride, and cyanocobalamin. The solution of vitamins and minerals is then added to the blend, with agitation.

An ascorbic acid solution, 12% solids, is prepared by combining the required amount of 45% KOH with cold ingredient water and adding the required amount of ascorbic acid. Once the pH is determined to be in the range of 6–10, the ascorbic acid solution is added, with agitation, to the blend.

The flavor solution is prepared by mixing the necessary amount of water, at a temperature of about 38°–49° C. (100°–120° F.), the artificial chocolate flavor, and artificial fresh cream. The flavor solution contains about 20% solids. The flavor solution is added, with agitation, to the blend.

The pH of the complete blend is adjusted to 6.6–6.8 with 1N KOH or 1N citric acid, placed in suitable container, such as 8 oz. metal cans, and terminally sterilized. After sterilization the pH of the complete blend is in the range of 6.4–6.6. Of course, if desired, the nutritional product may be manufactured using aseptic methods, and packaged in suitable containers. The nutritional product manufactured by the method described herein is a ready-to-serve liquid. However, it is understood to be within the scope of the present invention to provide a nutritional product that is a concentrated liquid or a powder.

While the nutritional product of the present invention has only been manufactured in liquid form, it is understood that it may be produced in powder form for later reconstitution with a suitable liquid without deviating from the scope of the present invention.

It is to be understood that the component(s) of the protein system of a nutritional product of the present invention comprising intact protein could comprise any suitable source of intact protein, such as pea protein and whey protein concentrate, whether in place of or in addition to the sodium caseinate. For example, if it were desired to reduce the pH of the nutritional product to a more acidic level, at which sodium caseinate is not stable, then a source of intact protein such as whey protein concentrate could be substituted for the sodium caseinate in an appropriate quantity.

An enteral nutritional product according to a second preferred embodiment has a protein system which comprises, by weight:
(a) about 60% of a soy protein hydrolysate;
(b) about 30% of a whey protein concentrate; and
(c) about 10% of a pea protein isolate.

An important feature of the nutritional product of this preferred embodiment of the present invention is the inclusion of pea protein isolate as a source of protein. Product has been manufactured using PISANE® PEA PROTEIN ISOLATE distributed by Cosucra SA of Momalle, Belgium. This commercially available pea protein isolate is a cream colored powder of particles having sizes of smaller than about 150 microns. Per the distributor's sales literature on a dry weight basis the pea protein isolate is: a minimum of 88% protein, a maximum of 0.2% fat, about 5% ash, and the pH of a 10% aqueous solution of the protein isolate is about 7.5. Per the distributor's sales literature functional properties of the pea protein isolate are: 60% minimum solubility at pH 7, 15% minimum solubility at pH 4.5, and 90% minimum emulsion stability (Oil/Water=40/60, 1% PISANE®, pH 3 to 7). Table 13 presents the average amino acids content of the pea protein isolate per the distributor's sales literature.

TABLE 13

AMINO ACIDS CONTENT OF PEA PROTEIN ISOLATE
(g/100 g proteins)

| | |
|---|---|
| Glycine | 4.3 |
| Alanine | 20.7 |
| Valine | 3.7 |
| Leucine | 7.7 |
| Isoleucine | 3.1 |
| Serine | 5.2 |
| Threonine | 3.8 |
| Tyrosine | 3.5 |
| Aspartic acid | 11.8 |
| Phenylalanine | 5.0 |
| Tryptophan | 1.0 |
| Proline | 4.4 |
| Methionine | 1.0 |
| Cysteine | 1.4 |
| Lysine | 7.5 |
| Histidine | 2.2 |
| Arginine | 7.7 |
| Glutamic acid | 20.7 |

The Bill of Materials for manufacturing a 1,000 pound batch of a nutritional product in accordance with this second preferred embodiment of the present invention is presented in Table 14. It is to be understood that this Bill of Materials is only an example for one flavor that has been manufactured and that functionally equivalent ingredients may be substituted into the Bill of Materials without deviating from the scope of the invention. It is believed that an enteral nutritional product according to this preferred embodiment of the invention has utility for providing enteral nutritional support for a person who is afflicted with cancer and is currently undergoing chemotherapy and/or radiation therapy.

TABLE 14

BILL OF MATERIALS

| INGREDIENT | AMOUNT PER 454 Kg BATCH | (1,000 LB) |
|---|---|---|
| Medium Chain Triglycerides (MCT) Oil | 1.785 kg | (3.932 lbs) |
| Canola Oil | 5.081 kg | (12.779 lbs) |
| Panodan ® (emuliffier) | 445.880 gms | |
| Oil Soluble Vitamin Premix: | 24.140 gms | |
| Vitamin A | 1.683 gms | |
| Vitamin D | 0.159 gms | |
| Vitamin E | 17.319 gms | |
| Vitamin K | 0.033 gms | |
| Vitamin A | 0.382 gms | |
| β-Carotene | 8.935 gms | |
| Iota Carrageenan | 68.040 gms | |
| Gum Arabic | 3.822 kg | (8.418 lbs) |
| Fish Oil | 0.892 kg | (1.966 lbs) |
| Water | 312.567 kg | (688.474 lbs) |
| Whey Protein Concentrate | 11.670 kg | (25.770 lbs) |
| Sodium Citrate | 1.724 kg | (3.797 lbs) |
| Magnesium Phosphate | 188.690 gms | |
| Calcium Carbonate | 433.240 gms | |
| Micronized Tricalcium Phosphate (TCP) | 0.848 kg | (1.867 lbs) |
| Maltrin ® 040 (maltodextrin) | 71.491 kg | (157.470 lbs) |
| Sucrose | 11.986 kg | (26.460 lbs) |
| Soy Protein Hydrolysate | 19.931 kg | (43.900 lbs) |
| Potassium Hydroxide 45% | 2.412 kg | (5.314 lbs) |
| Pea Protein Isolate | 3.723 kg | (7.210 lbs) |
| Zinc Sulfate | 8.628 gms | |
| Copper Sulfate | 1.717 gms | |
| Sodium Selenate | 0.075 gms | |
| Ascorbic Acid | 412.364 gms | |
| Choline Chloride | 70.000 gms | |
| Carnitine | 35.000 gms | |
| Taurine | 49.484 gms | |
| Niacinamide | 7.533 gms | |
| d-Ca Calcium Pantothenate | 4.885 gms | |
| Folic Acid | 0.064 gms | |
| Thiamine HCl | 1.186 gms | |
| Riboflavin | 0.972 gms | |
| Pyridoxine HCl | 1.200 gms | |
| Cyanocobalamin | 0.003 gms | |
| Biotin | 0.153 gms | |
| Artificial Vanilla | 2.270 kg | (5.000 lbs) |
| Mag 110 | 1.816 kg | (4.000 lbs) |

The nutritional product of this second preferred embodiment of the present invention may be manufactured using the ingredients from the above Bill of Materials of Table 14 by: (a) preparing several slurries/solutions which are then combined together; (b) heat processing the resultant blend; (c) adding vitamins, minerals and flavorings; and (d) packaging and sterilizing the resultant product.

An oil blend is prepared by the following procedure. The medium chain triglycerides (MCT) and canola oil are placed in a vessel and while being continuously agitated are heated to a temperature in the range of about 60°–65° C. (140°–150° F.). The product has been manufactured using fractionated coconut oil as the source of MCT, but any other suitable source of MCT may be used. Add the Panodan® (an emulsifier) to the resultant oil blend and allow it to dissolve therein before adding the remaining ingredients. Panodan distributed by Grinsted of Danisco, Denmark, (which also has a distributor located in Kansas, U.S.A.) is a diacetyl tartaric acid ester of mono-diglycerides, made from edible refried vegetable fat. Add the oil soluble vitamin premix, vitamin A, and β-carotene to the oil blend. Combine the iota carrageenan with the gum arabic, and add this mixture to the oil blend. Cool the oil blend to a temperature in the range of about 43°–49° C. (110°–120° F.). Add the fish oil to the oil blend, and maintain the oil blend at a temperature of about 43°–49° C. (110°–120° F.) under constant agitation until the oil blend is combined with other ingredients. The product has been manufactured using fish oil made from tuna and sardine meal, distributed by Mochida International of Shibuya-ku, Tokyo, Japan, but is produced and packaged by the Sambu-gun, Chiba plant of the Kyowa Technos Co., Ltd.

A whey protein-in-water slurry is prepared by the following procedure. About 66.30 kg (146.03 pounds) of water is placed in a vessel and heated to a temperature in the range of about 54°–60° C. (130°–140° F.). It is believed to be critical that the temperature of the water does not exceed 60° C. (40° F.) during this procedure. Add the whey protein concentrate to the water, and maintain the resultant protein-in-water slurry under agitation at a temperature of about 54° C. (130° F.) until this slurry is combined with other ingredients. The resultant slurry is about 15% total solids.

A carbohydrate slurry is prepared by the following procedure. About 141.309 kg (311.253 pounds) of water is placed in a vessel and heated to a temperature in the range of about 68°–74° C. (155°–165° F.). Dissolve the sodium citrate, magnesium phosphate, calcium carbonate, and micronized tri-calcium-phosphate (TCP) in the water. Preferably the micronized TCP has a maximum median particle size of about 2.2 microns as determined using a Cilas 715 granulometer or 1.0 micron as determined using a Sedigraph 500 ET particle size analyzer. To the resultant solution add the Maltfin® 040 (distributed by Grain Processing Company of Muscatine, Iowa, U.S.A.) and agitate the solution until the Maltrin® 040 is dissolved therein. Maltrin® 040 is a maltodextrin, or corn syrup solid. The number 40 refers to the dextrose equivalent of the ingredient (4 to 7) and was selected to minimize the effect of this ingredient on the osmolality of the nutritional product. To the resultant solution add to the sucrose and the soy protein hydrolysate. The resultant slurry should have a pH of about 4.3. Add 2.19 kg (4.814 lbs) of 45% potassium hydroxide to the slurry in an amount sufficient to adjust the pH of the slurry to be in the range of about 6.1–6.3. (If necessary the amount of 45% potassium hydroxide may exceed the amount specified). The slurry is maintained at a temperature in the range of about 54°–60° C. (130°–140° F.) under agitation until the slurry is combined with other ingredients. The resultant slurry is about 43% of total solids prior to the addition of the potassium hydroxide.

Just prior to combining the above described slurries/blends together, a pea protein-in-water slurry is prepared by the following process. About 29.46 kg (64.89 pounds) of water are placed in a vessel and heated to a temperature in the range of about 60°–65° C. (140°–150° F.). The pea protein is added to the water under agitation. The resultant slurry is maintained at a temperature of about 54° C. (130° F.) under agitation until this slurry is combined with other ingredients. The resultant slurry is about 10% total solids.

The oil blend, carbohydrate slurry, and first and second protein-in-water slurries are all combined together. The resultant final blend is then heat processed by the following procedure:

(a) The final blend is preheated to a temperature in the range of about 68°–74° C. (155°–165° F.).
(b) The final blend is de-aerated at 13–15 psi.
(c) The final blend is emulsified at 900–1100 psig.
(d) The final blend is heated to a temperature in the range of about 98°–106° C. (208°–222° F.) using a plate heater.
(e) The final blend is then heated to a ultra-high temperature in the range of about 146°–147° C. (294°–297° F.), and is held at this temperature for 5 seconds.
(f) The final blend is then flash cooled to a temperature in the range of about 98°–106° C. (208°–222° F.), then plate cooled to a temperature in the 71°–79° C. (160°–175° F.).
(g) The final blend is homogenized at 3900–4100/400–600 psig.
(h) The final blend is held at a temperature in the range of about 74°–85° C. (165°–185° F.) for 16 seconds.
(i) The final blend is then cooled to a temperature in the range of about 1°–70° C. (34°–45° F.), and held at this temperature until the product is sealed in containers (preferably within 48 hours).

An ultra trace mineral solution is prepared by the following procedure. About 0.42 kg (0.92 pounds) of water are placed in a vessel and heated to a temperature in the range of about 66°–71° C. (150°–160° F.). The zinc sulfate, copper sulfate and sodium selenate are then added to the water and the solution is agitated until these ingredients dissolve in the water. The resultant solution is about 20% total solids. The resultant solution is then added to the final blend.

A water soluble vitamin solution is then prepared by the following procedure. About 3.32 kg (7.303 pounds) of room temperature water is placed in a vessel. The ascorbic acid, 45% potassium hydroxide (0.23 kg (0.5 lbs)), choline chloride, carnitine, and taurine are added to the water with agitation. To the resultant solution the following vitamins are added: niacinamide, d-calcium pantothenate, folic acid, thiamine HCl, riboflavin, pyridoxine HCl, cyanocobalamin, and biotin. The resultant solution is about 20% total solids. The resultant solution is then added to the final blend. It is understood that in large scale production it would be preferable to have the water soluble vitamins provided in a premix.

A flavor solution is then prepared by the following procedure. About 72.14 kg (158.906 pounds) of room temperature water is placed in a vessel. The vanilla and MAG 110 (Monoammoniated Glycerrhizinate) are dissolved in the water. The resultant solution is about 5.4% of total solids. The flavor solution is then added to the final blend. The resultant final blend is about 29.3% total solids.

The final blend is then placed in suitable containers, such as 8 ounce cans, sealed with a suitable closure, and subjected to terminal sterilization.

It is recommended that if the enteral nutritional product of this second preferred embodiment is manufactured on a large scale that rather than adding the fish oil to the oil blend, the fish oil should be metered into the product blend at a constant rate just prior to emulsification to improve dispersion of the fish oil throughout the final blend.

We claim:

1. A liquid enteral nutritional product comprising: (a) protein system comprising, by weight, (i) at least 50% of a soy protein hydrolysate having a molecular weight partition as determined by size exclusion chromatography wherein 30–60% of the particles have a molecular weight profile in the range of 1,500–5,000 Daltons and the amino acid profile of the soy protein hydrolysate has about 0.4 to about 0.7% by weight free amino acids, and (ii) at least 10% intact protein; and (b) an emulsifier selected from the group consisting of diacetyl tartaric acid esters of mono-diglycerides and sodium stearoyl lactylate; the nutritional product having a pH in the range of 6.4 to 6.6 and being a stable emulsion after being subjected to terminal sterilization.

2. A liquid enteral nutritional product according to claim 1 wherein the intact protein comprises at least one intact protein selected from the group consisting of sodium caseinate, pea protein and whey protein concentrate.

3. A liquid enteral nutritional product according to claim 2 further comprising Iota carrageenan.

4. A liquid enteral nutritional product according to claim 2 further comprising Kappa carrageenan.

5. A liquid enteral nutritional product according to claim 1 further comprising Iota carrageenan.

6. A liquid enteral nutritional product according to claim 2 further comprising Kappa carrageenan.

7. A liquid enteral nutritional product according to claim 3 further comprising Kappa carrageenan.

8. A liquid enteral nutritional product according to claim 1 further comprising Kappa carrageenan.

9. A liquid enteral nutritional product according to claim 1 wherein the protein system comprises, by weight about 70–90% of the soy protein hydrolysate and about 10–30% sodium caseinate.

10. A liquid enteral nutritional product according to claim 9 further comprising 300–400 ppm of Iota carrageenan and 50–100 ppm of Kappa carrageenan.

11. A liquid enteral nutritional product according to claim 1 wherein the intact protein comprises pea protein and whey protein.

12. A liquid enteral nutritional product according to claim 11 wherein the emulsifier comprises diacetyl tartaric acid esters of mono-diglycerides.

13. A liquid enteral nutritional product according to claim 12 further comprising Iota carrageenan.

* * * * *

UNITED STATES PATENT AND TRADEMARK OFFICE
CERTIFICATE OF CORRECTION

PATENT NO. : 5,514,655
DATED : May 7, 1996
INVENTOR(S) : N. DeWille, T. Mazer, G. Snowden It is certified that error appears in the above-identified patent and that said Letters Patent is hereby corrected as shown below:

Amend Claim 6 by deleting "Claim 2" and inserting --Claim 5--

Signed and Sealed this

Twenty-fourth Day of September, 1996

*Attest:*

BRUCE LEHMAN

*Attesting Officer*  *Commissioner of Patents and Trademarks*